United States Patent [19]

Gruber et al.

[11] 4,293,714
[45] Oct. 6, 1981

[54] COPOLYMERIZABLE, ULTRAVIOLET LIGHT ABSORBER 4-ALKOXY-2'-ALLYLOXYBENZAZINES

[75] Inventors: Bruce A. Gruber, Worthington, Ohio; Donald H. Lorenz, Basking Ridge, N.J.

[73] Assignee: GAF Corporation, New York, N.Y.

[21] Appl. No.: 132,194

[22] Filed: Mar. 20, 1980

[51] Int. Cl.³ .......................................... C07C 109/04
[52] U.S. Cl. .................................. 564/249; 526/312; 424/59
[58] Field of Search ...................... 564/249; 526/312; 424/59

[56] References Cited

U.S. PATENT DOCUMENTS

| | | | |
|---|---|---|---|
| 2,440,070 | 4/1948 | Blount et al. | 564/249 |
| 3,235,595 | 2/1966 | Pawloski | 564/249 |
| 3,290,147 | 12/1966 | Mattor et al. | 564/249 |

*Primary Examiner*—Natalie Trousof
*Assistant Examiner*—L. Hendriksen

*Attorney, Agent, or Firm*—James Magee; Walter Katz

[57] ABSTRACT

This invention relates to copolymerizable ultraviolet light absorber compounds having the formula:

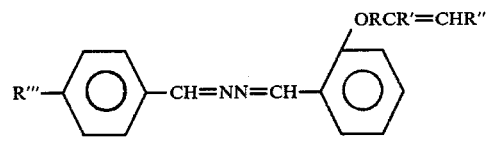

where:

R is alkylene oxyalkylene, alkyleneoxyalkylene or phenylene, which R groups are of up to 10 carbon atoms and are unsubstituted or substituted with hydroxy;

R' and R" are independently hydrogen or alkyl; $C_1$–$C_6$; and

R''' is alkyl $C_1$–$C_6$, substituted alkyl $C_1$–$C_6$, or alkoxy $C_1$–$C_6$.

10 Claims, No Drawings

COPOLYMERIZABLE, ULTRAVIOLET LIGHT ABSORBER 4-ALKOXY-2'-ALLYLOXYBENZAZINES

BACKGROUND OF THE INVENTION

1. Field of the Invention

This invention relates to novel copolymerizable ultraviolet light absorber compounds, and, more particularly, to 4-alkoxy-2'-allyloxybenzazine compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Still another limitation on the use of the prior art absorbers is that they provide little or no protection in the 300 to 400 nm region, which is a desirable region when the absorbers are used for skin and hair care products, such as sunscreen preparations and hair dye and hair tinting compositions.

Accordingly, it is an object of the present invention to provide novel copolymerizable ultraviolet light absorber compounds which are substantially free of the disadvantages of the prior art.

A particular object of this invention is to provide novel compounds which can be copolymerized directly with monomers, such as plastic material, to provide more permanent ultraviolet light protection.

A specific object is to provide ultraviolet light absorber compounds containing a copolymerizable ethylenic group.

These and other objects and features of the invention will be made apparent from the following more particular description of the invention.

SUMMARY OF THE INVENTION

What is provided herein are improved, novel copolymerizable ultraviolet light absorber compounds of the fomula:

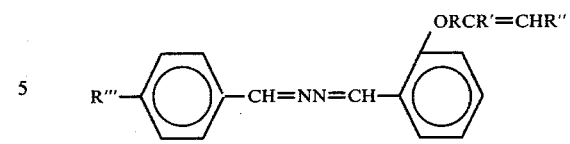

where R is alkylene $C_1$-$C_{10}$, oxyalkylene $C_1$-$C_{10}$, alkyleneoxyalkylene $C_1$-$C_{10}$, or phenylene $C_1$-$C_{10}$, unsubstituted or substituted with hydroxy, R' and R" are independently hydrogen or alkyl $C_1$-$C_6$, and, R''' is alkyl $C_1$-$C_6$, substituted alkyl $C_1$-$C_6$, or alkoxy $C_1$-$C_6$.

In the best mode of the invention, R is methylene, —$CH_2$—R' and R' are both hydrogen, and R''' is —$OCH_3$.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the absorber portion does not inhibit the copolymerization, and the ethylenic radical does not affect the light absorbing properties of the molecule.

The —RCR'=CHR" radical is copolymerizable with vinyl monomers so that the ultraviolet absorber becomes an integral part of the polymer. Suitable radicals are allyl, crotyl, methylpropenyl, vinylbenzyl, vinyloxyethyl, allyloxy-2-hydroxypropyl, and 2-hydroxy-3-butyenyl. The best mode is represented by allyl.

The novel compounds of the invention may be prepared from 4-alkoxy-2'-hydroxybenzazines by alkylation with an ethylenic halide.

The starting materials for the alkylation are obtained by condensing the commercially available substituted benzaldehydes with hydrazine. For example, p-methoxybenzaldehyde is condensed with hydrazine (1:1 molar ratio), followed by reaction with o-hydroxybenzaldehyde (1:1 molar ratio) (step a below).

The novel compounds of this invention are solids which are insoluble in water. The benzazine chromophore of the compounds herein has an ultraviolet absorbence peak at about 350 nm, but no visible absorbance.

The flow sheet below illustrates the reaction sequence for preparing the compounds of the invention.

Step (a)

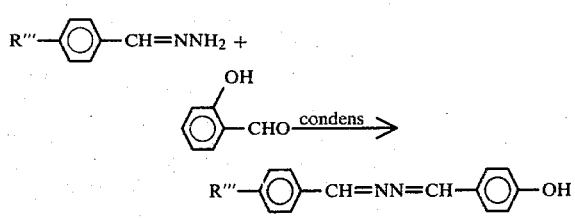

Step (b)

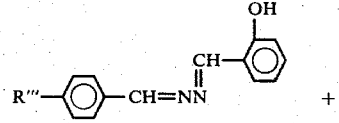

-continued $$ZRCR' + CHR'' \xrightarrow{\text{alkylai}}$$

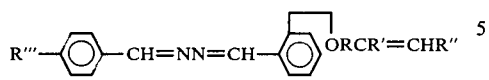

where Z is a halide and R', R" and R''' are as defined above.

Representative —RCR'—CHR" radicals are —CH$_2$—CH=CH$_2$ (allyl), —CH$_2$CH=CHCH$_3$ (crotyl), —CH$_2$C=CH$_2$ (2-methyl-1-propenyl),
    |
    CH$_3$ —CH$_2$—⟨O⟩—CH=CH$_2$ (vinylbenzenyl), —CH$_2$CH$_2$OCH=CH$_2$ (vinyloxyethyl), —CH$_2$CHCH$_2$OCH$_2$CH=CH$_2$, (3-allyloxy-2-hydroxypropyl,
    |
    OH and —CH$_2$CHCH=CH$_2$, (2-hydroxy-3-butenyl).
    |
    OH In step (a), the hydrazone is dispersed in ethanol with sodium acetate. The o-hydroxybenzaldehyde and acetic acid in ethanol are added with stirring until the azine separates. The product is filtered and the yield is nearly quantitative.

Step (b) involves alkylation of the hydroxy intermediate with a reactive ethylenic compound, such as an ethylenic halide, e.g. allyl chloride or allyl bromide. The reaction is carried out in an inert solvent, such as acetone, at a suitable temperature, generally at the reflux temperature of the solvent, for about 24 hours. The reactants are controlled to provide at least a 1:1 molar ratio of the ethylenic halide to the hydroxy compound.

The compounds of the invention may be copolymerized, for example, with monomers and oligomers by conventional free radical polymerization or with radiation curing, if desired, to provide useful polymeric coatings, or formulated into cosmetic preparations, such as skin and hair care products.

The following examples will describe the invention with more particularity.

EXAMPLE 1

4-Methoxy-2'-Allyloxybenzazine

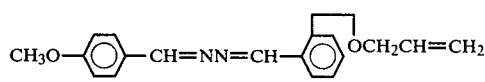

Step (a)

4-Methoxy-2'-Hydroxybenzazine

Into a flask equipped with a mechanical stirrer is charged 17.9 g (0.1 mole) of p-methoxyphenylhydrazone, 500 ml absolute ethanol and 12 g sodium acetate. To the rapidly stirred suspension then is added 20 ml absolute ethanol containing 12 g (0.1 mole) o-hydroxybenzaldehyde and 5 ml glacial acetic acid. The suspension is stirred for 1 hour, then filtered, giving 28 g (98%) of the solid product.

Step (b)

Into a flask equipped with a magnetic stirrer and reflux condenser is charged 11 g of 4-methoxy-2'-hydroxybenzazine, 300 ml acetone, 14 g potassium carbonate and 6.2 g (0.05 moles) of allyl bromide. The suspension is heated at reflux for 24 hours; then 300 ml water is added. Upon cooling an oil separates that quickly crystallizes. The solid is filtered giving 6 g (48%) of the product.

EXAMPLE 2

4-Methoxy-2'-Crotyloxybenzazine

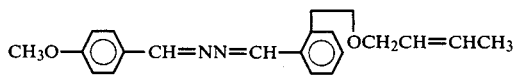

When crotyl bromide was substituted for allyl bromide in Example 1, the desired product is obtained.

EXAMPLE 3

4-Methoxy-2'-(2-Methylpropenyl)oxybenzazine

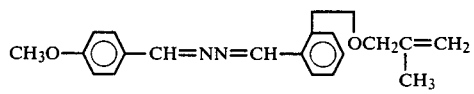

When 3-chloro-2-methyl-1-propene was substituted for allyl bromide in Example 1, the desired product is obtained.

EXAMPLE 4

4-Methoxy-2'-Vinylbenzyloxybenzazine

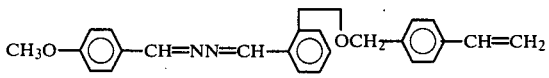

When vinylbenzyl chloride was substituted for allyl bromide in Example 1, the desired product is obtained.

EXAMPLE 5

4-Methoxy 2'-Vinyloxyethylbenzazine

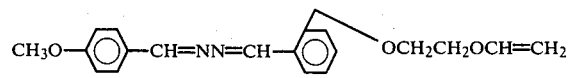

When vinyloxyethyl chloride was substituted for allyl bromide in Example 1, the desired product is obtained.

EXAMPLE 6

4-Methoxy-2'-(3-Allyloxy-2-Hydroxypropyl)oxybenzazine

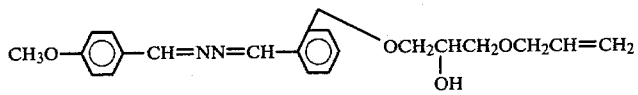

When 0.1 moles of (a) and allyl glycidyl ether, and, 250 mg. of tetramethylammonium chloride are heated at 150° C. for 16 hrs. diluted with 50 ml. methylene chloride, decolorized, filtered, and evaporated the desired product is obtained.

EXAMPLE 7

4-Methoxy-2'-(2-Hydroxy-3-Butenyl)oxybenzazine

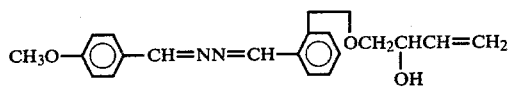

When 2-hydroxy-3-butenyl bromide was substituted for allyl bromide in Example 1, the desired product was obtained.

EXAMPLE 8

The monomer compound of Example 1 is copolymerized with another monomer by charging a flask with 150 ml ethanol, 1.5 g of 4-methoxy-2'-allyloxybenzazine and 50 g vinyl pyrrolidone. The contents are heated to 75° C. under $N_2$ and polymerization is initiated with 0.2 g azobis-isobutyronitrile (AIBN). After 1.5 hrs., another 0.2 g AIBN is added and heating is continued for another 1.5 hrs. The solvent is concentrated for another 1.5 hrs. The solvent is concentrated and added to stirred ether. A white precipitate of the copolymer is obtained which is filtered and dried, giving 18 g (36%) of product. A 5% aqueous solution of the copolymer is filtered; the ultraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. A copolymerizable ultraviolet light absorber compound having the formula:

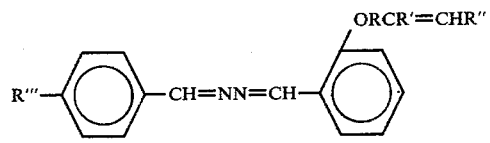

where R is alkylene, oxyalkylene, alkyleneoxyalkylene, said alkylene group being attached to the oxygen of the phenolic, or phenylene, which R groups are of up to 10 carbon atoms and are unsubstituted or substituted with hydroxy;

R' and R" are independently hydrogen or alkyl $C_1-C_6$; and,

R''' is alkyl $C_1-C_6$, or alkoxy $C_1-C_6$.

2. A compound according to claim 1 in which R''' is methoxy.

3. A compound according to claim 1 in which —RCR'=CHR" is allyl, crotyl, methylpropenyl, vinylbenzyl, vinyloxyethyl, allyloxy-2-hydroxypropyl, or 2-hydroxy-3-butenyl.

4. A compound according to claim 1 which is 4-methoxy-2'-alkyloxybenzazine.

5. A compound according to claim 1 which is 4-methoxy-2'-crotyloxybenzazine.

6. A compound according to claim 1 which is 4-methoxy-2'-vinylbenzyloxybenzazine.

7. A compound according to claim 1 which is 4-methoxy-2'-(2-methylpropenyl)oxybenzazine.

8. A compound according to claim 1 which is 4-methoxy-2'-vinyloxyethyloxybenzazine.

9. A compound according to claim 1 which is 4-methoxy-2'-(allyloxy-2-hydroxypropyl)oxybenzazine.

10. A compound according to claim 1 which is 4-methoxy-2'-(2-hydroxy-3-butenyl)oxybenzazine.

* * * * *